(12) United States Patent
Pilgeram et al.

(10) Patent No.: US 12,091,790 B2
(45) Date of Patent: *Sep. 17, 2024

(54) BRAIDED FILAMENT WITH PARTICULARIZED STRAND COMPOSITIONS AND METHODS OF MANUFACTURING AND USING SAME

(71) Applicant: Stryker Corporation, Kalamazoo, MI (US)

(72) Inventors: Kyle Craig Pilgeram, San Jose, CA (US); Luis Padilla, Katy, TX (US); Aaron Vodnick, East Greenwich, RI (US)

(73) Assignees: Stryker Corporation, Portage, MI (US); Cortland Cable Company, Inc., Cortland, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/153,717

(22) Filed: Jan. 12, 2023

(65) Prior Publication Data

US 2023/0151519 A1    May 18, 2023

Related U.S. Application Data

(60) Continuation of application No. 16/953,907, filed on Nov. 20, 2020, now Pat. No. 11,634,843, which is a
(Continued)

(51) Int. Cl.
*D04C 3/48*        (2006.01)
*A61B 17/06*       (2006.01)
(Continued)

(52) U.S. Cl.
CPC .......... *D04C 3/48* (2013.01); *A61B 17/06166* (2013.01); *A61B 90/92* (2016.02); *D04C 1/02* (2013.01); *D04C 1/06* (2013.01); *A61B 2017/0618* (2013.01); *A61B 2017/0619* (2013.01); *A61F 2/0811* (2013.01);
(Continued)

(58) Field of Classification Search
CPC ... D04C 1/02; D04C 1/06; D04C 3/48; D10B 2321/0211; D10B 2321/04; D10B 2509/04; D10B 2401/063
See application file for complete search history.

(56) References Cited

U.S. PATENT DOCUMENTS 3,681,510 A    8/1972 Lemieux
3,681,910 A *  8/1972 Reese .................... D02G 3/346
                                                  57/244

(Continued)

*Primary Examiner* — Bao-Thieu L Nguyen
(74) *Attorney, Agent, or Firm* — Lerner David LLP (57) ABSTRACT

In one embodiment, the present invention is a braided filament including a plurality of strands each having at least one ultrahigh molecular weight polyethylene fiber and at least one polyester fiber wherein the quantity of certain types of fibers in a first strand is the same as the quantity of the same type of fibers in a second strand. In a variant, one additional strand of the braided filament is a monofilament strand. In another variant, each strand is homogeneous with respect to the other strands and is made exclusively from ultrahigh molecular weight polyethylene fibers and polyester fibers such that each strand has the same distribution and quantity of fiber types.

20 Claims, 4 Drawing Sheets

Related U.S. Application Data continuation of application No. 16/208,979, filed on Dec. 4, 2018, now Pat. No. 10,870,935, which is a division of application No. 15/154,074, filed on May 13, 2016, now Pat. No. 10,167,582.

(51) Int. Cl.
- *A61B 90/92*   (2016.01)
- *D04C 1/02*   (2006.01)
- *D04C 1/06*   (2006.01)
- *A61F 2/08*   (2006.01)

(52) U.S. Cl.
CPC .. *D10B 2321/0211* (2013.01); *D10B 2331/04* (2013.01); *D10B 2401/063* (2013.01); *D10B 2509/04* (2013.01)

(56) References Cited

U.S. PATENT DOCUMENTS

| | | | |
|---|---|---|---|
| 3,949,755 A | 4/1976 | Vauquois | |
| 5,852,926 A | 12/1998 | Breedlove | |
| 5,901,632 A | 5/1999 | Ryan | |
| 6,161,400 A | 12/2000 | Hummel | |
| 6,341,550 B1 | 1/2002 | White | |
| 7,275,471 B2 | 10/2007 | Nishri et al. | |
| 7,329,271 B2 | 2/2008 | Koyfman et al. | |
| 7,360,477 B2 | 4/2008 | Hess | |
| 7,461,500 B2 | 12/2008 | Theis | |
| 7,703,371 B2 | 4/2010 | Morissette et al. | |
| 7,762,053 B2 | 7/2010 | Takada | |
| 7,784,258 B2 | 8/2010 | Hess | |
| 7,823,496 B2 | 11/2010 | Bosman et al. | |
| 8,012,172 B2 | 9/2011 | Grafton et al. | |
| 8,137,382 B2 | 3/2012 | Denham et al. | |
| 8,387,505 B2 | 3/2013 | Chou et al. | |
| 8,522,473 B2 | 9/2013 | Nakanishi | |
| 8,562,645 B2 | 10/2013 | Stone et al. | |
| 8,632,566 B2 | 1/2014 | Olson | |
| 8,789,452 B1 | 7/2014 | Janardhan et al. | |
| 8,801,783 B2 | 8/2014 | Stone et al. | |
| 8,832,992 B2 | 9/2014 | Nakanishi | |
| 8,883,302 B2 | 11/2014 | Zachariades et al. | |
| 9,078,644 B2 | 7/2015 | Stone | |
| 9,149,267 B2 | 10/2015 | Norton et al. | |
| 9,271,713 B2 | 3/2016 | Denham et al. | |
| 9,408,599 B2 | 8/2016 | Kaiser et al. | |
| 9,474,520 B2 | 10/2016 | Olson | |
| 9,492,158 B2 | 11/2016 | Stone et al. | |
| 9,642,661 B2 | 5/2017 | Stone et al. | |
| 9,681,940 B2 | 6/2017 | Stone et al. | |
| 9,757,119 B2 | 9/2017 | Norton et al. | |
| 9,918,827 B2 | 3/2018 | Berelsman et al. | |
| 10,092,288 B2 | 10/2018 | Denham et al. | |
| 10,167,582 B1 | 1/2019 | Pilgeram et al. | |
| 10,517,587 B2 | 12/2019 | Denham et al. | |
| 10,517,714 B2 | 12/2019 | Stone et al. | |
| 10,595,851 B2 | 3/2020 | Kaiser et al. | |
| 10,870,935 B2 * | 12/2020 | Pilgeram | D04C 1/02 |
| 11,634,843 B2 * | 4/2023 | Pilgeram | D04C 1/06 87/8 |
| 2002/0092414 A1 | 7/2002 | Nagaoka | |
| 2004/0267313 A1 | 12/2004 | Amery et al. | |
| 2005/0107797 A1 | 5/2005 | Romeo | |
| 2005/0192631 A1 | 9/2005 | Grafton | |
| 2010/0098948 A1 | 4/2010 | Nakanishi | |
| 2010/0160946 A1 | 6/2010 | Mirizzi et al. | |
| 2010/0192758 A1 | 8/2010 | Clough | |
| 2010/0274282 A1 * | 10/2010 | Olson | A61B 17/06166 87/8 |
| 2011/0111200 A1 | 5/2011 | Schneiders et al. | |
| 2011/0276040 A1 | 11/2011 | Quinn | |
| 2012/0285074 A1 | 11/2012 | Yang | |
| 2012/0297746 A1 | 11/2012 | Chou et al. | |
| 2013/0075978 A1 | 3/2013 | Azibert et al. | |
| 2013/0174719 A1 | 7/2013 | Chou et al. | |
| 2014/0088655 A1 * | 3/2014 | Stone | A61B 17/842 606/328 |
| 2014/0157973 A1 | 6/2014 | Plante | |
| 2014/0230634 A1 | 8/2014 | Nakai | |
| 2014/0260927 A1 | 9/2014 | Gilmore et al. | |
| 2015/0045831 A1 | 2/2015 | Allen | |
| 2015/0056449 A1 | 2/2015 | Broughton, Jr. et al. | |
| 2015/0128792 A1 | 5/2015 | Zachariades et al. | |
| 2015/0147379 A1 | 5/2015 | Albanna | |
| 2015/0247269 A1 | 9/2015 | Fukushima et al. | |
| 2015/0275409 A1 | 10/2015 | Owen | |
| 2016/0122918 A1 | 5/2016 | Tam et al. | |
| 2016/0122919 A1 | 5/2016 | Wagner et al. | |
| 2016/0168769 A1 | 6/2016 | McDonnell | |
| 2017/0239383 A1 | 8/2017 | Koyfman et al. | |
| 2017/0333176 A1 | 11/2017 | Stone et al. | |

\* cited by examiner

BRAIDED FILAMENT WITH PARTICULARIZED STRAND COMPOSITIONS AND METHODS OF MANUFACTURING AND USING SAME

CROSS-REFERENCE TO RELATED APPLICATIONS

This application is a continuation of U.S. application Ser. No. 16/953,907, filed Nov. 20, 2020, which is a continuation of U.S. application Ser. No. 16/208,979, filed Dec. 4, 2018 (U.S. Pat. No. 10,870,935), which is a divisional of U.S. application Ser. No. 15/154,074, filed on May 13, 2016 (U.S. Pat. No. 10,167,582), the disclosures of which are each incorporated herein by reference.

BACKGROUND OF THE INVENTION

Sutures are widely used for repair of tissue in the human body. For sutures to function as intended, they must have good tensile strength and exhibit non-slip properties. In many instances, they must also have acceptable knot-tying and knot-holding characteristics.

Sutures can be made from a variety of materials including, for example, polypropylene, polyester, polyamide, polyglycolide and polylactide. Further, ultra-high molecular weight polyethylene (UHMWPE) is a common material growing in popularity, particularly for sutures that must exhibit strength, such as those used for orthopedic procedures. A suture filament is manufactured by braiding strands together. Strands can be monofilaments or multifilaments. Monofilaments are known for their smooth, uniform surface. Such properties provide advantages including reduced tissue drag. However, monofilaments are disadvantageous relative to multifilaments in that they are generally stiff, difficult to tie and are less adept in their ability to secure a knot. Multifilament strands are typically manufactured into a substantially cylindrically shaped braid to form a suture, which can either be hollow or include a core. Individual multifilament strands are typically made by twisting individual fibers together. Although multifilament strands have advantages relative to monofilament strands, the type of fibers chosen for their performance characteristics can at the same time have an adverse impact in other ways. For example, using UHMWPE fibers can provide strength properties to the suture, but such fibers may also be prone to slippage.

Currently, obtaining a suture, also referred to as a filament, that possesses the strength properties obtained when using UHMWPE fibers while also obtaining the friction properties of polyester has required the braiding of individual, independent strands together to form a filament. However, such a braided construction might not properly distribute the benefits of each of the materials evenly throughout the resulting braided filament, and thus the performance properties shift in accordance with the relative change in the constitution of the filament. This problem is particularly apparent in orthopedic surgery, and in particular surgery involving use of filament structures under high levels of tension. For instance, the problem is particularly acute for ACL surgery. In such circumstances, obtaining the advantages of both UHMWPE and polyester, in a uniform and consistent manner throughout the filament, would be desirable.

Thus, there is a need for a suture, or braided filament, that can achieve concurrent improved performance respecting both strength and friction properties. At the same time, the filament should achieve such an improvement while also having the ability to function in a knotless fashion.

BRIEF SUMMARY OF THE INVENTION

The present invention generally relates to braided filaments, and methods of manufacture, assembly and use for the repair of soft and hard tissue. The braided filament of the present invention can include a plurality of strands where each strand has a select quantity and combination of fibers.

Specifically, in one embodiment, the invention relates to a braided length of filament including at least two strands braided with one another to form the filament. At least one of the at least two strands includes two or more fibers. Of the fibers, at least one of the fibers is UHMWPE and at least one of the other fibers is polyester. The quantity of UHMWPE fibers in a first strand can be equal to the quantity of UHMWPE fibers in a second strand. Similarly, the quantity of polyester fibers in a first strand can be equal to the quantity of polyester fibers in a second strand.

In a variant of this embodiment, the UHMWPE fibers in a first strand of the braided filament can include at least one first UHMWPE fiber and at least one second UHMWPE fiber of a weight different from the first UHMWPE fiber, along with at least one polyester fiber. In the same filament, a second strand can include at least one UHMWPE fiber and at least one polyester fiber. The UHMWPE fiber of the second strand can further be the first UHMWPE fiber or the second UHMWPE fiber of the first strand, or an UHMWPE fiber of a different weight.

In another embodiment, the braided filament includes one monofilament strand braided with the at least two strands to form the filament. The monofilament strand can include a color, marker, pattern, or any combination, such that the monofilament strand visibly contrasts with the at least two strands or provides a texture benefit.

In another aspect, the invention relates to a method of forming a braided filament. In a first embodiment of this method, a braiding machine is obtained to perform braiding. The braiding machine includes a plurality of carriers onto which a plurality of bobbins are loaded. When loaded, each bobbin includes a strand positioned thereon. Of the strands positioned on the bobbins, at least one strand comprises a strand that includes two or more fibers. At least one of the two fibers is UHMWPE and at least one of the other fibers is polyester. The braiding machine braids the strands together to form the braided filament.

Where one strand of the braided filament comprises at least one fiber of UHMWPE and at least one fiber of polyester, another strand of the braided filament can include the same number of UHMWPE fibers and polyester fibers as the one strand. Placed onto a bobbin, the strand on a first bobbin can further include at least one fiber of a first UHMWPE, at least one fiber of a second UHMWPE, and at least one fiber of polyester. On the same braiding machine, a strand on a second bobbin can include at least one fiber of UHMWPE and at least one fiber of polyester. This arrangement can further include a braiding machine where a first portion of the bobbins include strands as described for the first bobbin above and a second portion of the bobbins include strands as described for the second bobbin above. For example, the first portion can be about half of the bobbins and the second portion can be the remainder of the bobbins.

The fibers of a strand can be plied together in a side-by-side, twisted, commingled or served configuration.

Braiding of the strands using the braiding machine can be performed by moving the plurality of bobbins in a pre-defined pattern relative to one another to braid the plurality of strands. In a typical braiding machine, a first portion of bobbins moves in a clockwise position, while a second portion of bobbins moves in a counterclockwise position. For instance, the first portion of bobbins can be "A bobbins" and the second portion of bobbins can be "B bobbins," where all of the A bobbins are positioned in the clockwise locations and all of the B bobbins are positioned in the counterclockwise locations. The pattern of braiding can in this instance include alternatingly passing A bobbins and B bobbins to generate a braid having the pattern ABABAB with respect to loading bobbins onto carriers wherein the loading process presents the operator with one clockwise carrier followed by one counterclockwise carrier and so on and so forth. Other patterns are also envisioned.

In another embodiment of this method, a braiding machine is obtained to perform braiding. The braiding machine includes a plurality of carriers onto which a plurality of bobbins are loaded. When loaded, each bobbin includes a strand positioned thereon. Of the strands positioned on the bobbins, at least one strand comprises a monofilament strand or a strand that includes two or more fibers. Where the strand includes two or more fibers, at least one of the two fibers is UHMWPE and at least one of the other fibers is polyester. The braiding machine braids the strands together to form the braided filament.

Yet another aspect of the invention is a method of forming a one-way adjustable filament structure. In one embodiment, this method includes obtaining a braiding machine having a plurality of carriers onto which a plurality of bobbins are loaded. At least one bobbin includes a strand positioned thereon. At least one strand includes two or more fibers, wherein at least one of the fibers is of a material different from at least one of the other fibers. Using the braiding machine, the strands are braided together to form a braided filament. The filament includes a hollow core along its length where the length is defined as extending between first and second ends of the filament. To form the one-way adjustable filament structure, one of the first or second ends is passed into the core, along at least a portion of the length of the core and then is passed out of the core.

The method described can further include the step of passing the other of the first and second ends into the core, along at least a portion of the length of the core, and out of the core. This forms a second one-way adjustable filament structure. The portion of the core through which the first end passes and the portion of the core through which the second end passes are preferably spaced from one another along the length of the braided filament. The fibers of the strands used to braid the filament can include at least one UHMWPE fiber and at least one polyester fiber.

DETAILED DESCRIPTION

The various structures, devices, assemblies, and associated methods of use, manufacture and assembly, of the present invention are intended for use in the repair, reattachment, replacement or otherwise securement of tissue. This includes both hard tissue and soft tissue. Soft tissue may be, for example, meniscus, cartilage, capsule, ligaments and tendons, replacement grafts of any of these soft tissue, or the like. Hard tissue is considered to be bone. While many of the exemplary embodiments disclosed herein are directed towards the ultimate use of the filament structures as a tissue anchor for implantation into a bone tunnel, such as in anterior cruciate ligament (ACL) replacement and repair, other uses are also envisioned. As used herein, "proximal" or "proximally" means closer to or towards an operator, e.g., surgeon, while "distal" or "distally" means further from or away from the operator.

The term braid as used throughout is intended to refer generally to a pattern of strands. In a braided arrangement, the strands form a length of filament. The term "filament" as used throughout includes a plurality of strands and is intended to refer generally to a plurality of braided strands forming a suture or other thread-like material which may have a hollow core along at least a portion of its length. Preferably, the "filament" is a braided suture having a hollow core along its length. The term "continuous" as used throughout is intended to refer generally to a single length of material, or preferably, a single length of braided, hollow suture.

The term "strand" as used throughout is intended to refer generally to a sub-structure of the braided filament made from a plurality of fibers. In addition to the fibers, the strands may further contain other components such as coatings and the like. In other words, a plurality of fibers form a strand, and a plurality of strands form a braided filament.

While as used herein a plurality of fibers form a strand, a strand may alternatively be formed of a single monofilament strand. The term monofilament strand as used throughout is intended to refer generally to a strand including a single fiber. Conversely, the term strand or multifilament strand as used throughout is intended to refer generally to a strand including a plurality of fibers.

The term "fiber" as used throughout is intended to refer generally to elongated bodies of indefinite length having a length dimension much greater than its width and thickness. Examples of fibers include but are not limited to a string, ribbon, strip and tape. Fibers can have a regular or irregular cross-section.

The term "homogeneous" as used throughout is intended to refer generally to a comparison between strands. One strand is homogeneous with another if its fiber composition is the same as in the other strand. An example of homogeneous strands would be two strands, where each strand includes two UHMWPE fibers and one polyester fiber.

Figure 1:
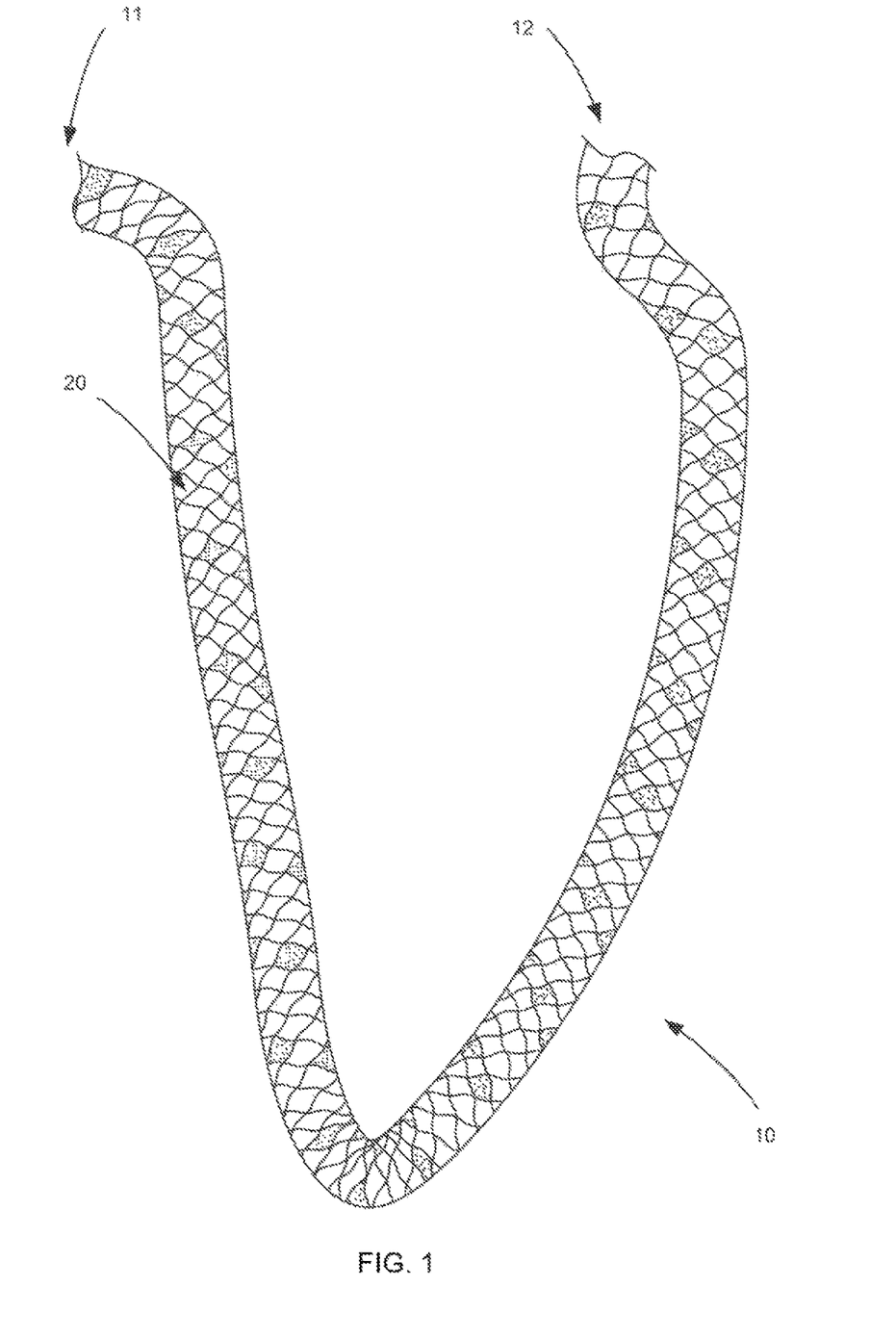
FIG. 1 illustrates one embodiment of a braided filament.

In one aspect, the invention relates to a braided length of filament. FIG. 1 illustrates a filament 10 in accordance with one embodiment of the invention. The length of filament 10 is constructed from materials that are plied together to form the filament. The filament may be constructed from materials such as, but not limited to, polyester, polyethylene (including ultra-high molecular weight polyethylene (UHMWPE)), polytetrafluorethylene (including expanded polytetrafluorethylene), nylon, polypropylene, aramids (such as Kevlar®-based materials), polydioxanone, polygycolic acid, liquid crystal polymer (LCP), organic material (silk, animal tendon, or the like), metallic wire, or any combination of these materials. Preferably, the length of filament 10 is composed of braided suture. At least one strand 20 of the filament includes at least one UHMWPE fiber and at least one polyester fiber.

The filament 10 includes a first end 11 and second end 12. In the embodiment illustrated in FIGS. 1-3, the filament 10 includes sixteen strands. The strands can be dyed partially or entirely using various colors to aid in identifying, during use, the filament 10 from another filament, the first end 11 from the second end 12, or the like.

The strand pattern forming a filament is identified by "pick count," defined in terms of "picks per inch." The pick count is the number of strands along a specific line along the length of the braid for a specified unit of measure, traditionally one inch. Typical pick counts for the braided filaments of the present invention are between about 20 and about 100 picks per inch, preferably about 30 to about 60 picks per inch, and more preferably about 35 picks per inch. The pick count must be balanced between a lesser pick count (e.g., looser braid, easier to manufacture, increased strength, worse cyclic performance) and a high pick count (e.g., tighter braid, better cyclic performance, more difficult to manufacture, reduced strength, more difficult to manipulate and/or splice).

The diameter of the filament 10 varies depending on the intended application for the filament, number of strands used, and fiber material used. However, the diameter of the braided filament 10 varies widely and may be any diameter known to those of skill in the art. The braided filament 10 can have a cross-section that is circular, round, flat, oblong, or the like.

Figure 2:
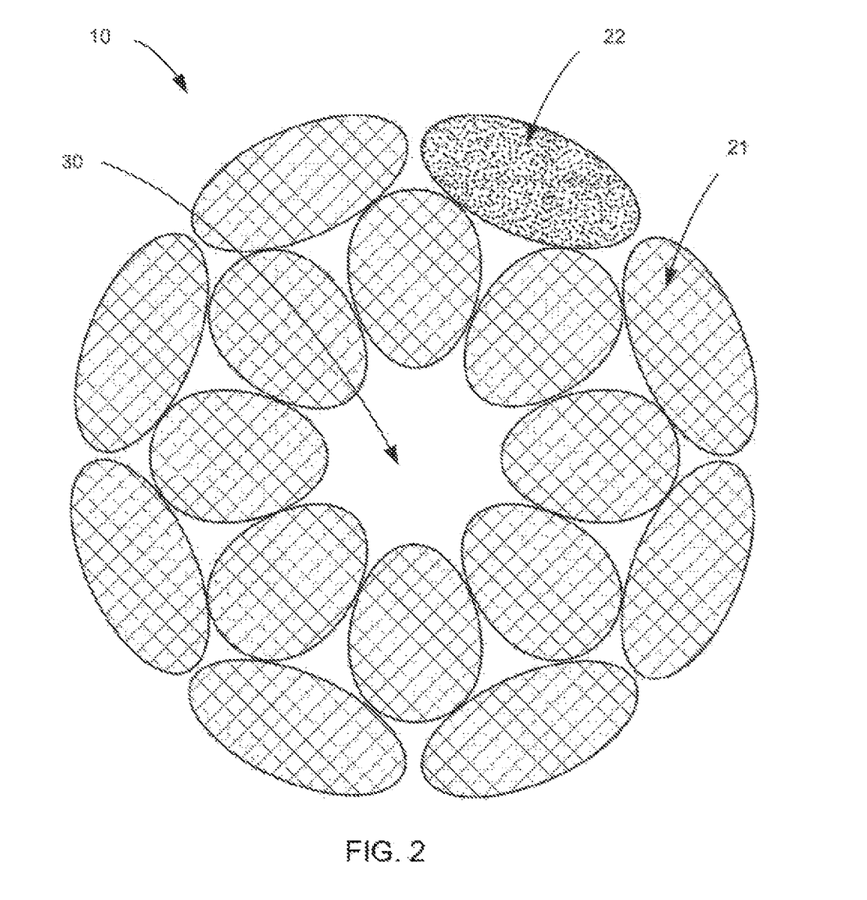
FIG. 2 illustrates a sectional view of the braided filament of FIG. 1.

As illustrated in FIG. 2, the filament 10 includes sixteen strands 21, 22. While it is preferable to have all of the strands in the filament 10 include multiple fibers, FIG. 2 is illustrated as including strand 22 as a monofilament strand and the others are multifilament strands 21 for illustrative purposes and for ease of reference of certain variations of this invention that are envisioned.

Figure 3:
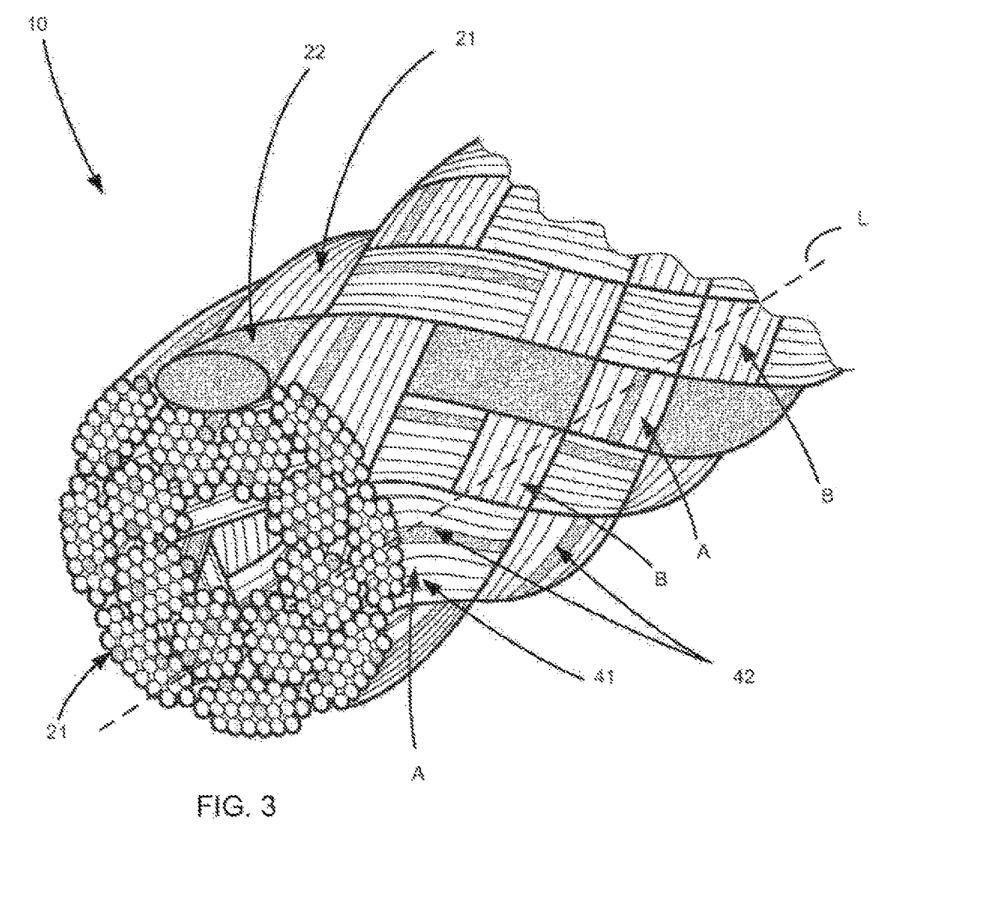
FIG. 3 illustrates a perspective view including section of the braided filament of FIG. 1.

As shown in FIGS. 2 and 3, the monofilament strand 22, if present, is of unitary construction and can be made from polyester material or any other material desired. The monofilament could alternatively be comprised of UHMWPE or other filament materials described herein. The monofilament strand 22 is woven with other strands 21 to form a braided filament 10. The monofilament can have a unique identifier in the form of a marking. Marking can be accomplished through use of a material with a unique pattern or through marking the monofilament with an identifiable pattern.

The multifilament strands can have any number of fibers as desired. For example, as shown in FIG. 3, the multifilament strands 21 can include approximately twenty four fibers. The outer bounds of each multifilament strand 21 are outlined in bold in the figure. Typically, as an example, the quantity of fibers in a strand is between eighteen and thirty-six. All of the strands 21 shown comprise entirely of UHMWPE fibers and polyester fibers. As shown, for purposes of illustration in FIG. 3, the aforementioned strands 21 include two polyester fibers 42 with the remainder being UHMWPE fibers 41. The ratio of UHMWPE to polyester fibers can vary and is not limited by the illustration. The UHMWPE fibers can be further divided into more than one unit of weight per length of material, commonly known in the art as "denier." More specifically, for example, certain of the UHMWPE fibers can be 100 denier UHMWPE while certain of the polyester fibers can have the same denier or a different denier. As a further example, other UHMWPE fibers in a strand and/or braid can have a different denier from the 100 denier UHMWPE fibers.

Further, in a variant of the above embodiment, one strand can include the same quantity and combination of fibers as another strand. Where two or more strands share common material compositions in this way, they are known as homogeneous strands as described herein. For example, where one strand includes a quantity "A" of UHMWPE fibers and a quantity "B" of polyester fibers, one or more of the other strands in the filament that includes the same A UHMWPE fibers and B polyester fibers is homogeneous with the first strand. This strand matching can also apply where the denier of the fibers varies. For example, where one strand includes a quantity "A" of a first denier UHMWPE fiber, a quantity "B" of a second denier UHMWPE fiber different from the first denier UHMWPE fiber, and a quantity "C" of a first denier polyester fiber, one or more of the other strands in the filament can also have the same combination of "A," "B," and "C" fibers. The strands can further be divided into homogeneous groups. For example, eight of sixteen strands of a filament each include a quantity A of a first denier UHMWPE fiber and a quantity B of a first denier polyester fiber. In the same filament, the other eight strands can each include a quantity X of a first denier UHMWPE fiber, a quantity Y of a second denier UHMWPE fiber and a quantity Z of a first denier polyester fiber. As discussed above, the actual denier of each of the quantities of fibers can differ between the first group of strands and second group of strands.

In another variant of the above embodiment, fewer than all of the multifilament strands 21 of the filament 10 comprise entirely of a combination of UHMWPE fibers and polyester fibers. For example, one strand includes fibers selected only from UHMWPE and polyester material, and the remaining strands can include fibers made from any filament materials known in the art and as described herein, including UHMWPE fiber and polyester fiber.

In another variant, each multifilament strand 21 includes one or more UHMWPE fibers and one or more polyester fibers. Other fibers that can be used in addition to UHMWPE and polyester include those made from filament materials known in the art and as described herein.

In yet another variant, at least one multifilament strand 21 of the filament includes one or more UHMWPE fibers and one or more polyester fibers. Other fibers that can be used in addition to UHMWPE and polyester include those made from filament materials known in the art and as described herein.

In the alternative, at least one multifilament strand 21 of the filament includes fibers made exclusively from UHMWPE 41 and polyester 42 and at least one other multifilament strand 21 includes fibers made exclusively from UHMWPE.

In another embodiment, sixteen strands, each having at least two fibers, form a filament. In this way, no monofilament strands are included in the filament. The particular fibers and combinations of fibers used for this embodiment can be any described in the above embodiments or the like. In a variation of this embodiment, a larger or smaller number of strands may be used.

In another embodiment, a filament includes two or more monofilament strands and at least one multifilament strand. At least one of the at least one multifilament strands includes one or more UHMWPE fibers and one or more polyester fibers.

In another embodiment, the number of fibers in a first strand is different from the number of fibers in a second strand. Any number of strands can have a unique quantity of fibers. For example, three strands can have thirty fibers, two strands can have eighteen fibers and the remaining strands can have twenty eight fibers. The number of fibers in a particular strand can also, in some cases, exceed thirty or in other cases, total less than eighteen.

In yet another embodiment, a strand is disposed in the hollow core of the braided filament. The strand can be any strand described herein. For example, the strand can be a monofilament strand or a multifilament strand. The materials of the strand can be any described above. Alternatively, multiple strands can be braided and then disposed in the hollow core of the primary braided filament. In other words, such a strand or strands becomes a separate core within the hollow core of a certain length of the outer braided filament.

In another embodiment, the composition of homogeneous strands is determined based on the percentage of overall material constituted by a particular fiber. In this way, the homogeneous strands would all include the same percentage of various fibers. For example, where twenty four fibers are used to form each strand, a design requirement is specified requiring that each strand include approximately 15% polyester. To achieve this, each strand includes four polyester fibers. If the other fibers used in these strands are all UHMWPE, for example, each of these strands can be said to be homogeneous to one another. This approach to strand material can be applied in other ways as well. For example, a certain percentage of monofilament strands can be required to form a filament. Another example could be that each strand includes no more than 25% of fibers that are not UHMWPE or polyester.

In any of the above embodiments, the total number of strands of the filament can be less or greater than sixteen as sixteen is simply an exemplary number. For example, the filament can include fourteen strands or eighteen strands or any other number as desired. Additionally, an odd number of strands may be incorporated into a filament. Typically, an even number of strands results in a substantially cylindrical filament while an odd number of strands results in a substantially flat or ovular filament.

In any of the above embodiments and in all variants, the filament 10 includes at least two strands. At least one strand of the two strands includes at least one UHMWPE fiber and one polyester fiber. Beyond this requirement, the fibers of each strand may include any combination of fibers including any combination of UHMWPE fibers and polyester fibers. These combinations are not limited in any way by the denier values of the particular fibers used.

In another embodiment, the present invention is a method of forming a braided filament. This method is performed using a braiding machine, for example, an exemplary braiding machine as disclosed in U.S. Pat. No. 1,356,570, the disclosure of which is incorporated by reference herein as if fully set forth herein. In this example, the typical braiding machine includes a plurality of carriers. Each carrier includes a bobbin. The exemplary braiding machine of the '570 patent includes a cover plate that supports a plurality of carriers. In this example, each carrier includes a carrier post, a carrier base connected to the post and a carrier disk, though other machines are also known which may be used in the present invention. Continuing with this example, the carrier posts carry a plurality of bobbins. Mounted on the carrier base is a post. The post includes a vertical bar guide, a central guide, and a loop guide attached at the top. The posts are located adjacent to respective bobbins to allow for manufacture of braided filaments.

Each bobbin is loaded with a strand for use in manufacturing a filament. In operation, continuing the example of a 16-strand filament, eight of the sixteen carriers in the example of the '570 patent move about the machine in a clockwise direction while the remainder moves counterclockwise. The carriers move relative one another in a desired pattern as described further below. For example, the strand from the bobbin passes over the vertical bar guide and then through the central guide on the post. From the guide the strand is carried through a rigid loop guide and thereafter around a hook guide on a drum. From the drum the strand is carried to a rigid guide on the base of the carrier and from there to the loop guide. From the loop guide, the strand travels to the braiding location to be braided with other strands.

In one embodiment, a braiding machine is supplied with strands placed on bobbins of the machine. For strands that are not monofilament strands, each strand includes at least two fibers (as discussed above) that are plied together. The at least two fibers can be plied together in a side-by-side, twisted, commingled or served configuration, or other configuration. A side-by-side configuration requires fibers to be plied such that they are positioned adjacent and parallel to one another. Twisting involves, for example, twisting fibers to the right in a Z twist or to the left in an S twist. The respective center sections of the letters Z or S are indicative of the slope of the fibers in the strand once plied together in a twist. Commingling is also known as interlacing, tangling, entangling, mingling and intermingling. Commingling can also involve intramingling. Commingling can be achieved in a variety of ways. For example, one approach involves separate fibers that are caused to revolve about an intermediate axis or axes at different speeds or in different directions so that interlacing occurs. In another, separate fibers are rotated randomly and alternately along their lengths in velocity gradients or by rolling on a solid surface or surfaces and the fibers are then brought together to be intermingled by unwinding of different fiber twists in the frictional contact. A served configuration is created by plying the fibers in a helical shape. A helix is a curve in three dimensions aligned so that a tangent at any point is at a constant angle relative to an axis. Strand materials are otherwise made using fiber counts and from materials as described above.

The braiding machine braids a desired number of strands to form a filament. For example, a braiding machine can braid sixteen strands using sixteen bobbins. It is noted that, typically, an even number of strands forms a more cylindrical filament while an odd number of strands forms a more planar filament. While the example herein utilizes an even number of strands to form cylindrical filaments, embodiments using an odd number of strands (to make flat filaments) are also envisioned.

In operation, the braiding machine first causes the plurality of bobbins to move. At this time, the machine unwinds strands to be braided. The strands are braided into a filament by weaving the strands together to form the length of the filament 10. The type of braiding performed by the braiding machine can be any braid known to those of skill in the art. For example, as shown in FIG. 1, through braiding, the strands are woven in a manner that leaves a hollow core 30 in the center of the cross section of the filament, as visible in FIG. 2.

Once the strands are braided into a braided filament 10, the filament may undergo finishing processes and is then prepared for storage and subsequent use. Finishing processes might include, for example, pre-tensioning via a single or cyclic loading process, such as is described in U.S. patent application Ser. No. 14/561,889, filed Dec. 5, 2014, the entirety of which is incorporated by reference herein as if fully set forth herein. Such pre-tensioning processes may tighten the braid and limit future stretching and lengthening of the suture following implantation and once placed under tension within the patient. Such future stretching and lengthening could decrease the effectiveness and stability of the repair and lead to failure or limited use of the repaired tissue by the patient. Storage of the suture may include, for example, the braided filament being directed to tensioning rollers and thereafter to a final take-up spool where the stock filament is systematically wound in uniform layers about the spool. The filament can be cut into desired lengths prior to final packaging, at a later manufacturing step, or at any other time desired. Alternatively, the braided suture could undergo a further manufacturing step to form a particular suture configuration, one such configuration described below and illustrated in FIGS. 4A-4C. Any pre-tensioning or other finishing step, if included, can occur before or after forming such suture configurations.

In one variant, the bobbins of the braiding machine can braid the strands into a pattern. The pattern can be between one braid relative to another braid.

For example, in one embodiment, two types of strands are used, strand A and strand B. Strand A includes either a monofilament strand or at least two fibers where one fiber is UHMWPE and the other fiber is polyester. Strand B is based on the same requirements as strand A, but is different from strand A either in fiber number or material, or both.

In one embodiment, the bobbins of the braiding machine braid the strands into a pattern wherein strand A and strand B bobbins are alternatingly positioned in locations to move in a clockwise direction, and again, strand A and strand B bobbins are alternatingly positioned in locations to move in a counterclockwise direction. This configuration, where A and B bobbins can be found in both clockwise and counterclockwise positions, form a pattern AABBAABBAABB and so on until all strands are braided. This braiding pattern is illustrated as an example in FIG. 3, whereby along line L, the A strands and B strands alternate with one another.

The bobbins of the braiding machine braid the strands into a pattern wherein strand A bobbins are positioned to move in a clockwise direction and strand B bobbins are positioned to move in a counterclockwise direction. in this configuration, the braiding pattern of the filament is based on a clockwise rotation of all strand A bobbins and counterclockwise rotation of all strand B bobbins throughout the braiding process to generate a pattern ABABAB and so on until all strands are braided to form a filament of a desired length (or such filament can be continuous and later be cut into desired lengths). This braiding pattern would result in a different pattern (not shown) from that in FIG. 3 whereby, for example, along a line L (similar to that illustrated in FIG. 3) there would only be either a repetition of strand A or a repetition of strand B, but not both.

In another embodiment, the pattern of strands used to braid the filament can be any combination of strand A and strand B that can be made with the combinations available based on the total number of strands used, including using an odd number, or different number of A and/or B bobbins.

In still another variant, additional strand varieties may be included to braid a filament. For example, the braiding pattern can involve positioning strand A, strand B, and strand C bobbins as desired into the clockwise and counterclockwise locations in order to generate a pattern such as, for example, ABCABCABCABC. As above, any available order of strands may be used to form the braiding pattern when three or more strand varieties are used.

In any of the above embodiments, strands can be monofilament strands or include a plurality of fibers. Where the strands include a plurality of fibers, the quantity and type of fibers can be any described herein. However, at least one strand will include a UHMWPE fiber and a polyester fiber.

In another embodiment, machine components other than bobbins can be used to the extent they are known in the art for the purposes of braiding the strands into a filament.

In addition to the advantages described above, this method produces filaments with improved strength over filaments of the prior art without the need for specialized braiding machinery.

The braided filaments and methods of manufacture described herein have numerous advantages. When compared to prior art filaments, the filaments as described herein exhibit improved performance under cyclic loading. Including both UHMWPE and polyester fibers into individual strands more evenly distributes the two materials throughout the filament to provide the strength properties of UHMWPE and the added friction of the polyester throughout, which likewise balances out the undesired aspect of UHMWPE (lower friction or higher "slipperiness") and polyester (lower strength). In other words, the combination of UHMWPE and polyester materials used within a strand, and its use in multiple strands in a homogeneous manner, provides the advantages of both strength and friction properties to be more consistent along the length of the filament.

The strength properties of the invention described herein make the present invention particularly advantageous for use in ACL repair or other medical procedures involving high tensile forces, such as orthopedic repairs. The filament as described herein can also be adapted to a variety of loop types when used in surgery. For example, it is beneficial in adjustable loops as well as in knotless loops and applications.

Figure 4A:
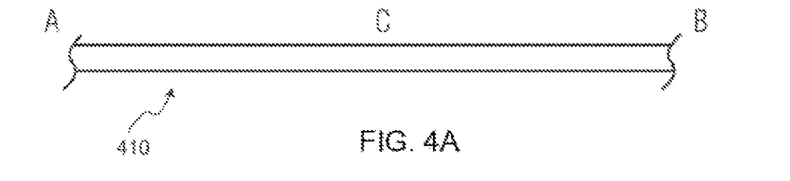
FIGS. 4A, 4B and 4C illustrate one embodiment of an adjustable filament structure.
Figure 4B:
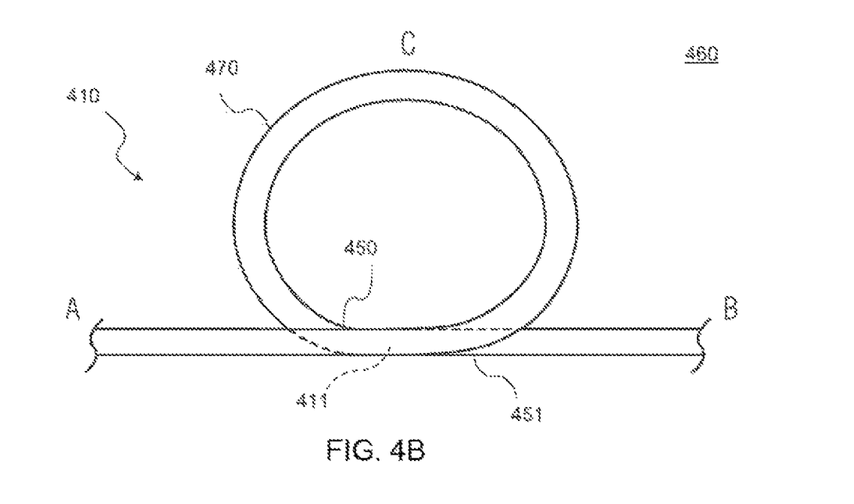
Figure 4C:
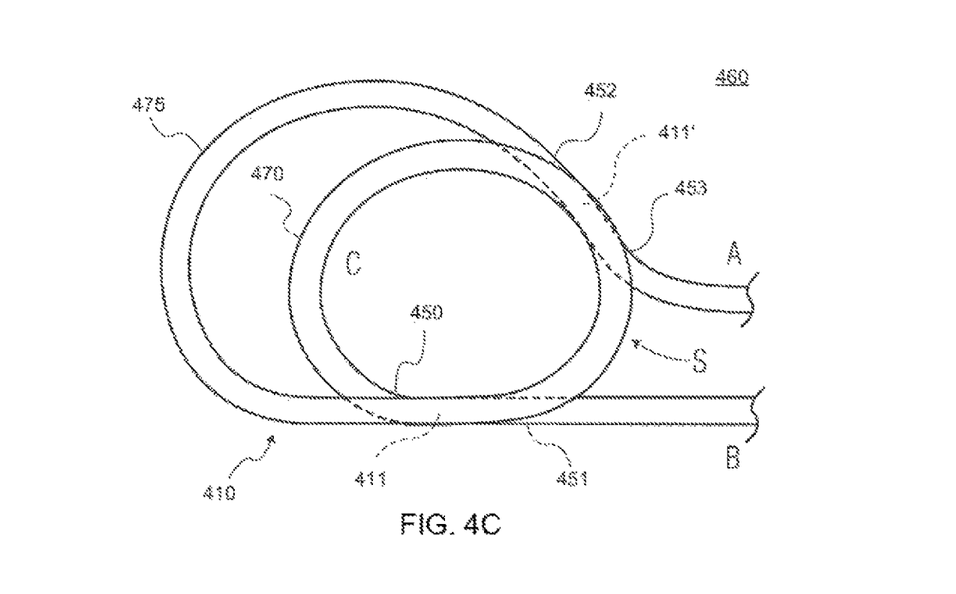

For example, one embodiment of an adjustable loop structure for use in ACL repair is illustrated in FIGS. 4A-4C. In this embodiment, the filament is configured into a one-way adjustable loop filament structure. Referring to FIGS. 4A-4B, one embodiment of an adjustable, continuous filament structure 410, and a method of assembly thereof, is illustrated. The filament structure is formed of a single, continuous length of filament 410, illustrated in FIG. 4A. The filament 410 has a first free segment terminating at first end A, a second free segment terminating at second end B, and a middle portion C. The filament structure 410 includes at least one continuous, adjustable loop portion 470, as illustrated in FIG. 4B. The filament structure can also include, as illustrated in FIG. 4C, a second continuous, adjustable loop portion 475. Each adjustable loop portion 470, 475 is adjustable through manipulation of each end A, B (as illustrated, loop portion 470 is continuous with the second free segment terminating in end B and loop portion 475 is continuous with the first free segment terminating in end A).

Each loop portion 470, 475 is formed by end A, B being passed through a portion of the filament 410, as discussed in greater detail below. In one embodiment of assembling filament structure 460, as illustrated in FIGS. 4B-5C, the filament 410 is generally formed into a loop, and as illustrated in FIG. 4B, the end B is passed into an inner core 411 of the body of the filament 410 at a first position 450. The entrance into the inner core 411 at first position 450 is preferably a gap in the braiding of the filament 410, though the first position 450 (or any of the other "positions" referenced herein) could be prepared using a needle or other tool to form an opening for passage of end B. The end B can then continue to be passed through at least a portion of the inner core and withdrawn from the inner core at a second position 451. Such a configuration results in the first adjustable loop 470 that is adjustable by the free segment ending in end B.

The second adjustable loop 475 can be formed in a similar manner, as illustrated in FIG. 4C, in which the free segment ending in end A is introduced into the inner core 411' of the filament 410 at a third position 452 (inner core 411' and inner core 411 can be part of a continuous inner core throughout the entire length of the filament 410 or can be individual portions of a partially hollow filament 410 such that the inner core does not extend along the entire length of the filament). The end A can then continue to be passed through at least a portion of the inner core and withdrawn from the inner core at a fourth position 453. Such a configuration results in the second adjustable loop 475 that is adjustable by the free segment ending in end A. In between the first position 450 and the third position 452 is generally formed the saddle S, though second position 451 and fourth position 453 could be one in the same, such that saddle S is not present. In any event, during adjustment of the first and/or second loops 470, 475, the location of the first, second, third and fourth positions (and saddle S if present) will largely not be altered (aside from potentially deforming or stretching/crushing as the free segments pass through the inner cores 411, 411' of these filament portions), and thus this portion of the filament structure 460 remains largely stationary.

While in the illustrated example of FIG. 4C the entry and exit positions of the free segments into the inner core of the filament are separate from one another, in another variation, for example, the first position 450 and either of the third or fourth positions 452, 453 could be one in the same, and likewise, the second position 451 could be one in the same as either of the third or fourth positions 452, 453. In such a variation, the first and second free segments would at least partially overlap within the inner core of the filament. While such overlap could increase the friction and thus the stability of the filament structure, such a configuration would also increase the bulk along that portion of the filament.

The ends A, B can be passed into, passed through, and withdrawn from the inner core of the filament by any known method. Preferably, for example, a splicing needle (not shown), as is known in the art, is used to pass the ends A, B into and through the inner core of the filament. However, other instrumentation, methods or manufacturing processes can be used as desired.

As discussed above, if the filament structure 460 is formed during manufacture, the formed filament structure can also then undergo the further manufacturing step of pre-tensioning (if desired or required) which may increase stiffness and reduce extension under load, and specifically, under cyclic load. In other words, a pre-tensioned filament structure may exhibit less stretch once implanted in the patient, where it undergoes cyclic loading as the patient uses the repaired tissue. Further, such a pre-tensioned filament is stiffer, and thus can be manipulated in ways that a filament, prior to pre-tensioning, cannot be manipulated—for example, a pre-tensioned filament structure may be able to be pushed through a portion of anatomy, or the like.

It should be noted that the method disclosed and envisioned in FIGS. 4A-4C may be performed as an arthroscopic procedure and/or as a minimally invasive technique, and further, while the repair may be used on any tissue for reattachment to another tissue, the above discussed method is focused on the repair or replacement of an ACL in a knee joint of a patient.

Filament structure 460 is advantageous for such methods of surgery because of the simplicity of the design in that the filament structure includes two adjustable loops, each adjustable through a single free segment. Further, the adjustable loop portions are continuous and made from an overall single strand as well, which lessens the possibility of entanglement, e.g., within the narrow bone tunnels for ACL surgery and/or during various anatomical locations. Additionally, because the filament structure is constructed by splicing a single length of filament, the construction is strong and durable and requires no additional components, thereby reducing the likelihood of failure.

Filament structure 460 is one such structure that can particularly benefit from the advantages of the inventive braided filament disclosed herein, and as such will be used as one illustrative example for a novel braided filament of the present invention. In designing such a filament structure 460 for use in ACL repair (e.g., for positioning within a bone tunnel to connect the replacement ACL graft to a "button anchor" positioned on the lateral aspect of the femur, as known in the art), the required strength characteristics of UHMWPE must be weighed against the necessity of the filament having adequate friction to maintain the one-way locking within inner cores 411, 411' that is required for a successful repair. Moreover, such a repair also includes size limitations as the bone tunnel should be as small as possible and the "fixed" distance, defined in FIG. 4C as extending from first position 450, through second and fourth positions 451, 453 and saddle (if present), and to second position 452, should likewise be as short as possible. Such limitations require that the resulting braided filament have high strength while maintaining a relatively small shape as well as exhibiting high friction while limiting contact between the inner core 411, 411' and the end portions adjacent ends A, B.

In light of these parameters, and the desire to utilize UHMWPE and polyester fibers as the base materials for the braided filament, it was discovered that filaments formed of strands each containing some UHMWPE fibers and some polyester fibers provided the required strength and friction characteristics while keeping within the size and "fixed" distance limitations. Conversely, braided filaments formed of strands containing only UHMWPE and other strands of only polyester failed either in strength or friction, and/or required excessive size and/or fixed length to remedy such failings.

For instance, in comparing a braided filament of the present invention, where each strand included at least one UHMWPE fiber and at least one polyester fiber, to a braided filament where at least one of the strands included only polyester (as is normally found in the art), with all other dimensions being largely equal (e.g., about 35 to about 40 picks per inch and a length of "tucked" inner core 411, 411' of about 18 picks each), the latter braid failed to achieve the necessary strength requirements (failed at about 500 N) while the former braid was markedly above the strength requirements (over 800 N).

Continuing with the above example, other variables were also deemed of importance. For instance, as discussed above, the AABBAABB pattern of strand braiding resulted in, looking along a specific line "L" along the length of the surface of the braided filament, as in FIG. 3, the strand types (or picks) alternate A-B-A-B, and include 35 picks per inch as shown. Both of the analyzed exemplary braids above used the AABBAABB pattern. As such, this braiding pattern may evenly disperse the strand types along the length of the braided filament, which may result in additional uniformity throughout the braided filament and more uniform filament characteristics. The aforementioned ABABAB results in, along a similar line L, a continuous line of strand A-A-A-A (or B-B-B-B), which may have benefits in other braided filaments though resulted in inferior results in this exemplary analysis.

In another example, the way the fibers in each strand interact with one another and are plied may also affect performance. For example, twisting fibers within a strand may result in improved characteristics, though adjacent strands may require opposing twisting directions to counteract any potential torque within the strand once under cyclic loading.

Based on the example illustrated in FIG. 3, the homogenous strands of the present invention allow for more even distribution of the polyester fibers throughout the UHMWPE fibers, resulting in enhanced characteristics beneficial to braided filaments, particularly those that undergo cyclic loading as in the case of support for an ACL graft (e.g., filament structures such as those illustrated in FIGS. 4A-4C).

Other embodiments of adjustable filament structures that can include such braided filaments disclosed herein are described in the aforementioned U.S. patent application Ser. No. 14/561,889.

In another embodiment, a sliding knot can be formed using two braided filaments as described herein. The sliding knot can be any known to those of ordinary skill in the art.

In yet another aspect, the filament of the present invention is used as a knotless filament structure that can affix soft tissue to bone. The filament can be used for any knotless filament structure known to those of ordinary skill in the art.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of forming a one-way adjustable filament structure, comprising the steps of:
    obtaining a filament comprising a plurality of independent strands braided with one another to form the filament, the filament having a length defined between a first end and a second end and a hollow core along at least a portion of the length, wherein, at least one strand includes a plurality of fibers, and wherein at least one of the plurality of fibers of the at least one strand is ultrahigh molecular weight polyethylene (UHMWPE) and at least one of the other fibers of the at least one strand is polyester; and
    passing the first end into the core, along at least a portion of the length of the core, and out of the core to form the one-way adjustable filament structure.

2. The method of claim 1, further comprising adjusting the one-way adjustable filament structure, after the passing step, by pulling on the first end.

3. The method of claim 1, further comprising a second passing step comprising passing the second end into the core, along at least a portion of the length of the core, and out of the core to form a second one-way adjustable filament structure.

4. The method of claim 3, further comprising adjusting the second one-way adjustable filament structure, after the second passing step, by pulling on the second end.

5. The method of claim 3, wherein the first and second ends respectively pass through first and second portions of the core, wherein the first and second portions of the core are spaced from one another along the length of the braided filament.

6. The method of claim 1, wherein the plurality of fibers of the at least one strand are plied together in a side-by-side, twisted, commingled, or served configuration.

7. The method of claim 1, wherein the at least one strand has a greater number of UHMWPE fibers than polyester fibers.

8. The method of claim 1, wherein the at least one strand comprises the same number of UHMWPE fibers as at least one of the other strands, and wherein the at least one strand comprises the same number of polyester fibers as the at least one of the other strands.

9. The method of claim 1, wherein at least one of the other strands comprises a monofilament strand.

10. The method of claim 9, wherein the monofilament strand includes a color, marker, pattern, or any combination thereof, such that the monofilament strand contrasts with the at least one strand.

11. A method of forming a one-way adjustable filament structure, comprising the steps of:
    obtaining a filament comprising a plurality of independent strands braided with one another to form the filament, the filament having a length defined between a first end and a second end and a hollow core along at least a portion of the length, wherein, at least one strand includes a plurality of fibers, and wherein the at least one strand has a greater number of UHMWPE fibers than polyester fibers; and
    passing the first end into the core, along at least a portion of the length of the core, and out of the core to form the one-way adjustable filament structure.

12. The method of claim 11, further comprising adjusting the one-way adjustable filament structure, after the passing step, by pulling on the first end.

13. The method of claim 11, further comprising a second passing step comprising passing the second end into the core, along at least a portion of the length of the core, and out of the core to form a second one-way adjustable filament structure.

14. The method of claim 13, further comprising adjusting the second one-way adjustable filament structure, after the second passing step, by pulling on the second end.

15. The method of claim 13, wherein the first and second ends respectively pass through first and second portions of the core, wherein the first and second portions of the core are spaced from one another along the length of the braided filament.

16. The method of claim 11, wherein the plurality of fibers of the at least one strand are plied together in a side-by-side, twisted, commingled, or served configuration.

17. The method of claim 11, wherein the at least one strand comprises the same number of UHMWPE fibers as at least one of the other strands, and wherein the at least one strand comprises the same number of polyester fibers as the at least one of the other strands.

18. The method of claim 17, wherein the at least one strand is homogeneous with the at least one of the other strands.

19. The method of claim 11, wherein at least one of the other strands comprises a monofilament strand.

20. The method of claim 19, wherein the monofilament strand includes a color, marker, pattern, or any combination thereof, such that the monofilament strand contrasts with the at least one strand.

* * * * *